United States Patent [19]
Edwards

[11] Patent Number: 6,151,711
[45] Date of Patent: Nov. 28, 2000

[54] WELDING HELMET WITH REMOVABLE FACE PLATE AND LENS CARTRIDGE

[75] Inventor: David B. Edwards, Sandy, Utah

[73] Assignee: Jackson Products, Inc., Chesterfield, Mo.

[21] Appl. No.: 09/283,489

[22] Filed: Apr. 1, 1999

[51] Int. Cl.[7] ........................................... A61F 9/06
[52] U.S. Cl. ............................................... 2/8
[58] Field of Search ................................ 2/8, 9, 15, 11; 219/147

[56] References Cited

U.S. PATENT DOCUMENTS

| | | | |
|---|---|---|---|
| 2,152,865 | 4/1939 | Bowers | 2/8 |
| 2,726,395 | 12/1955 | Anderson | 2/8 |
| 3,444,561 | 5/1969 | Boyer | 2/8 |
| 4,774,723 | 10/1988 | Ruck | 2/8 |
| 5,224,219 | 7/1993 | Edwards et al. | 2/8 |
| 5,533,206 | 7/1996 | Petrie et al. | 2/8 |

FOREIGN PATENT DOCUMENTS

| | | | |
|---|---|---|---|
| 704714 | 2/1954 | United Kingdom | 2/8 |

OTHER PUBLICATIONS

Brochure on Speedglas® 9000 by Hornell, date unknown.

*Primary Examiner*—Michael A. Neas
*Attorney, Agent, or Firm*—Howell & Haferkamp, LC

[57] ABSTRACT

A welding helmet includes a removable lens cartridge assembly which is slidingly received by a slot at the front of the welding helmet. The lens cartridge assembly includes a picture frame slot into which a face lens may be friction fit by insertion from the side. Additional filters and lenses may be held in place within the cartridge by a removable frame assembly that has a plurality of integrally formed but resilient finger extensions which press against the filters as they are placed within the cartridge. The frame assembly mechanically interlocks with the removable cartridge with a plurality of locating tabs and slots. The cartridge assembly itself is also mechanically positively interlocked to the welding helmet with a locating nib and receiving hole near the bottom of the slot. The receiving slot has a front and rear picture frame border which surrounds and encapsulates the removable lens cartridge so that the lens cartridge is mechanically locked in place and captured within a mechanical fixture to avoid its being dislodged upon impact.

24 Claims, 3 Drawing Sheets

WELDING HELMET WITH REMOVABLE FACE PLATE AND LENS CARTRIDGE

BACKGROUND AND SUMMARY OF THE INVENTION

Welders' masks or helmets are known in the prior art and have been used for years to protect the face and head of a welder as he welds. One such example of a welder's mask is found in U.S. Pat. No. 1,601,830 issued Oct. 5, 1926, the disclosure of which is incorporated herein by reference. Generally, welders' helmets include a lens area through which the welder views his work as he welds. There have been many developments with respect to these lens packs including auto darkening lenses, special filter lenses, and other various lens systems for special purpose welding and the like. Traditionally, these lens packs include an outer protective cover lens, a middle light filtering lens for protecting the welder's eyes from the intense light generated during welding, and a rear cover lens. With the new auto darkening electronic lens packages, a protective outer or cover lens is provided and the electronic lens package is generally held in place with some type of spring loaded structure or otherwise to accommodate its being removed. However, it is not believed that any prior art welder's helmet provides for the ready removal and replacement of all of the lenses contained within a traditional lens pack, an electronic auto darkening lens package including cover lens, or the like, or that the techniques and structure used for holding these lens packs are particularly adapted to their ready changeout as might be desired when a welder moves from one type of welding to another.

In order to solve these and other problems found in the prior art, and as an advancement in the art of welders' helmets, the inventor has succeeded in designing and developing a welding helmet having a removable face plate assembly, the face plate assembly comprising a cartridge for sliding insertion into a slot in the helmet with an interlocking mechanical latch mechanism for securing the cartridge in place. The cartridge itself has a picture frame slot accessible from the side of the cartridge into which a protective cover lens may be slidingly inserted for protecting the other lenses contained within the cartridge. The cartridge also includes a removable frame which has a plurality of retention clips which are integrally formed with the frame but resilient so as to provide a spring pressure against additional lenses which the frame holds in place immediately behind the face lens. The frame itself is held in place by a plurality of tabs and slots in the sides of the cartridge and frame so that the frame may be mechanically positively secured within the cartridge and avoid its inadvertent release therefrom which might otherwise discharge the lenses from the cartridge and cause their damage. This is undesirable both to avoid the expense of damage to what may be very expensive lenses as well as a safety hazard which might be encountered should the welder be welding and the protective lenses inadvertently fall out of their desired shielding orientation within the cartridge in front of the welder's face and eyes. Additionally, the receiving slot in the face of the welder's mask provides for the cartridge to be inserted at the top of the slot with the bottom of the slot providing a mechanical step for the cartridge to prevent its falling down and out of the welder's helmet. Furthermore, an extended lip surrounds the periphery of the slot opening which matches and lines up with the frame so that the frame is mechanically captured within the cartridge when the cartridge is inserted and locked in place within the welder's helmet.

Thus, the present invention allows for a welder to readily remove the lens cartridge by merely separating a nib and hole which releases the cartridge for being lifted out of its slot. Once removed, a second cartridge may already be prepared with different lenses to accommodate the welder's desire to change to different lenses, or some other application merely by slipping the second cartridge into the slot and securing it with the nib and hole. Furthermore, should the protective face lens be damaged by flying debris, it may be readily replaced by removing the cartridge and removing the face lens by sliding it sideways out of its receiving slot with a replacement face lens being inserted by reversing the process. Should the welder desire merely to maintain his same cartridge and yet remove and replace lenses, this is readily achieved by removing the frame from the cartridge by disengaging the tabs and slots in the sides of the cartridge and frame which permits access directly to the lenses for their removal and replacement.

The present invention provides ready access, removability, and replacement capabilities for the face lens and other protective lenses commonly found in a welding helmet without the use of tools, in a quick and easy fashion, without hampering or compromising the desired safety and reliability of the welding helmet itself.

While the principal advantages and features of the present invention have been briefly explained, a fuller understanding of the invention may be gained by referring to the drawings and Description of the Preferred Embodiment which follow.

DETAILED DESCRIPTION OF THE PREFERRED EMBODIMENT

Figure 1:
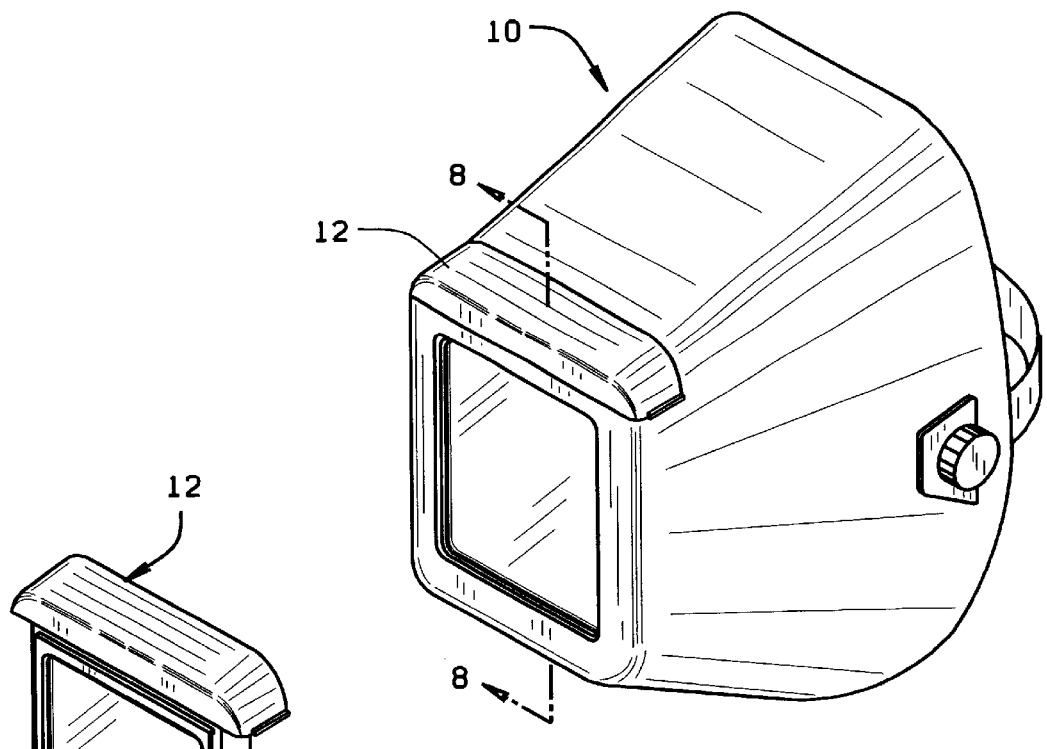
FIG. 1 is a perspective view of a welding helmet of the present invention with removable lens cartridge.
Figure 2:
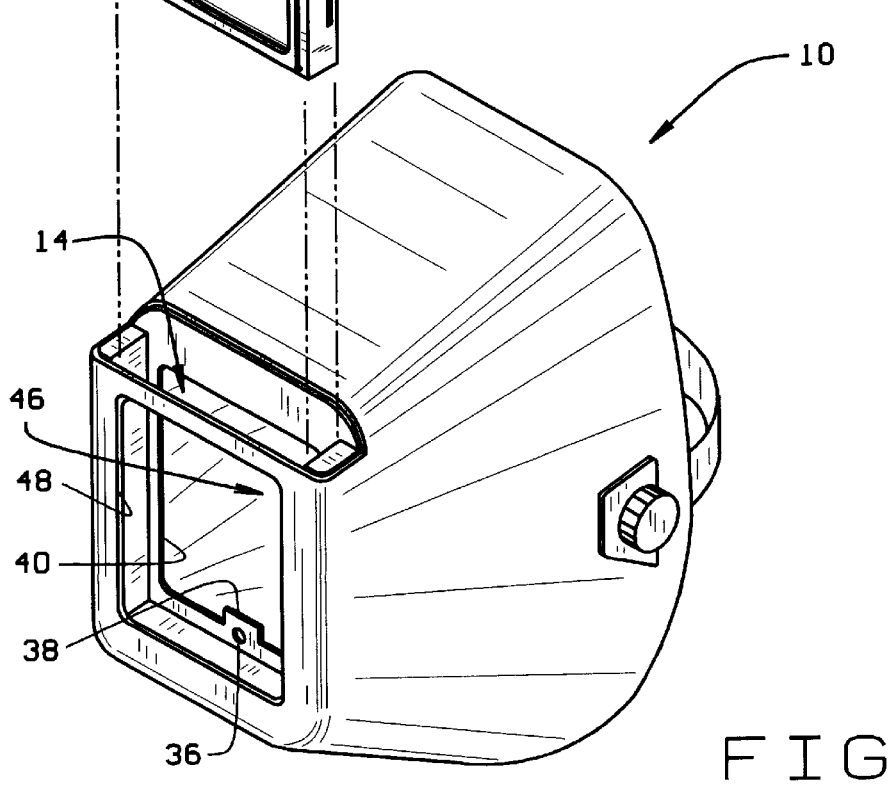
FIG. 2 is a perspective as shown in FIG. 1 with the removable lens cartridge separated and lifted from its receiving slot in the welding helmet.

As shown in FIGS. 1 and 2, a welding helmet 10 includes a removable lens cartridge 12 which is slidingly received within a slot 14 at the front of the welding helmet 10.

Figure 3:
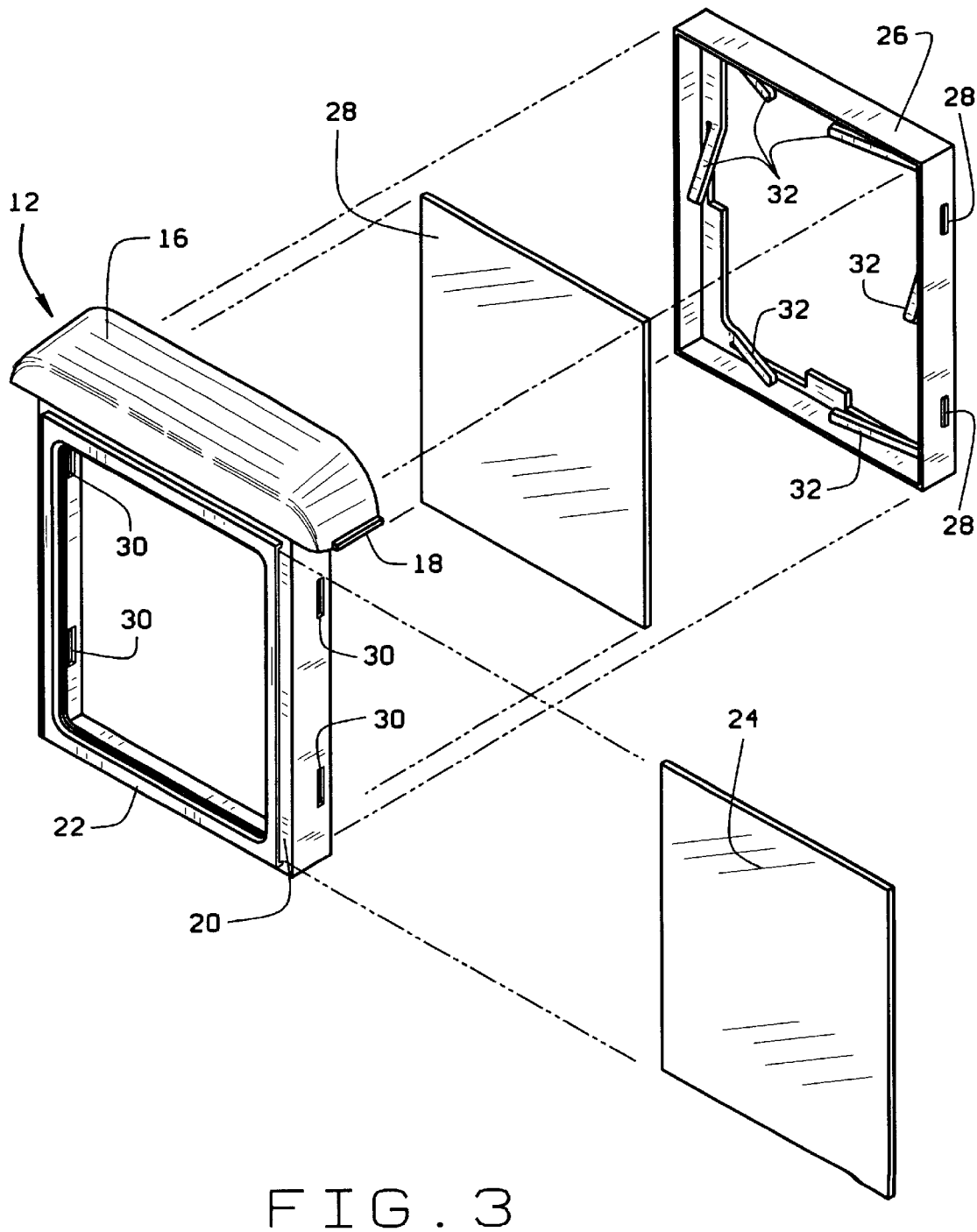
FIG. 3 is an exploded view of the cartridge assembly detailing the face lens slot for receiving the face lens and the frame for holding protective filters in place within the cartridge.
Figure 4:
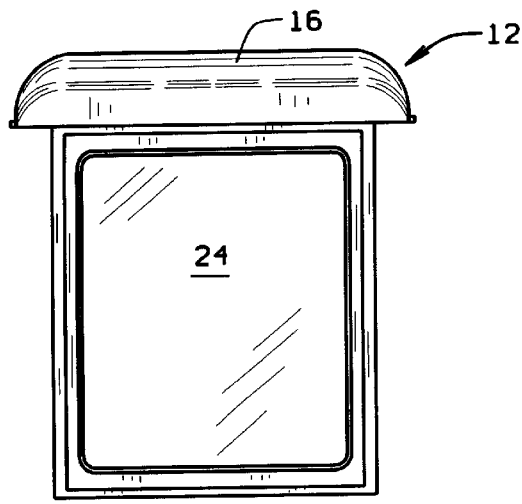
FIG. 4 is a front view of the lens cartridge.
Figure 5:
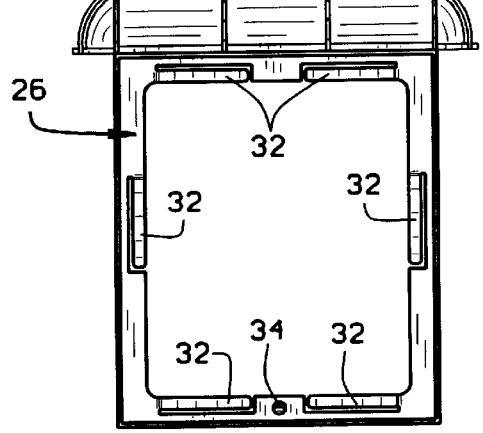
FIG. 5 is a rear view of the lens cartridge.
Figures 6, 7:
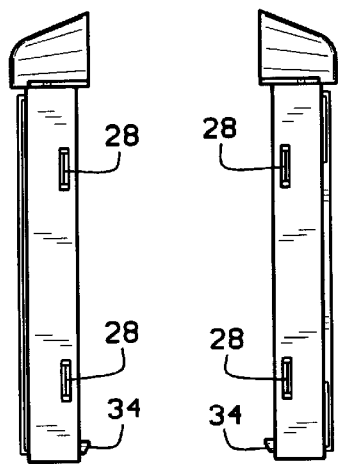
FIG. 6 is a left side view of the lens cartridge.
FIG. 7 is a right side view of the lens cartridge.

As shown in FIG. 3, the cartridge 12 is generally in the shape of a rectangular picture frame assembly with a "top hat" 16 which matches and lines up with the general contour of the welding helmet 10. Included is a finger tab 18 at one side of the top hat 16 which provides a convenient place for a welder to apply an upward push on the cartridge 12 and dislodge it from slot 14 when it is desired to be removed. At the front of cartridge 12 is a picture frame slot 20 formed between a generally rectangularly shaped picture frame member 22 integrally formed and molded with the cartridge 12. A face lens 24 may be conveniently slidingly inserted from the side of the cartridge 12 and held with a friction fit within slot 20, all as depicted in FIG. 3. At the back of cartridge 12 is a frame assembly 26 which, when assembled into the cartridge, captures one or more filters or lenses 28 within cartridge 12. The frame assembly 26 mechanically interlocks within cartridge 12 by means of a plurality of tabs 28 and associated slots 30. These tabs 28, of which four are shown on frame assembly 26, and slots 30, of which four are shown in cartridge 12, locate the frame assembly 26 within the cartridge 12 and provide a positive mechanical interlock therebetween. Frame assembly 26 has a number of fingers 32 integrally formed with frame assembly 26 and which are biased at an oblique angle so that when frame assembly 26 captures one or more filters 28 within cartridge 12 by interlocking tabs 28 with slots 30, the fingers 32 resiliently urge the one or more filters 28 against and into the front of cartridge 12 to hold them in a fixed orientation. It should be noted that the cartridge 12 including frame assembly 26 as well as the welding helmet 10 may be made from suitable plastic materials which are low weight and impact resistant, as known to those of ordinary skill in the art. As such, these plastic parts may be formed in any variety of ways, including injection molding such that the cartridge 12, frame assembly 26, and welding helmet 10 are integrally formed.

Figure 8:
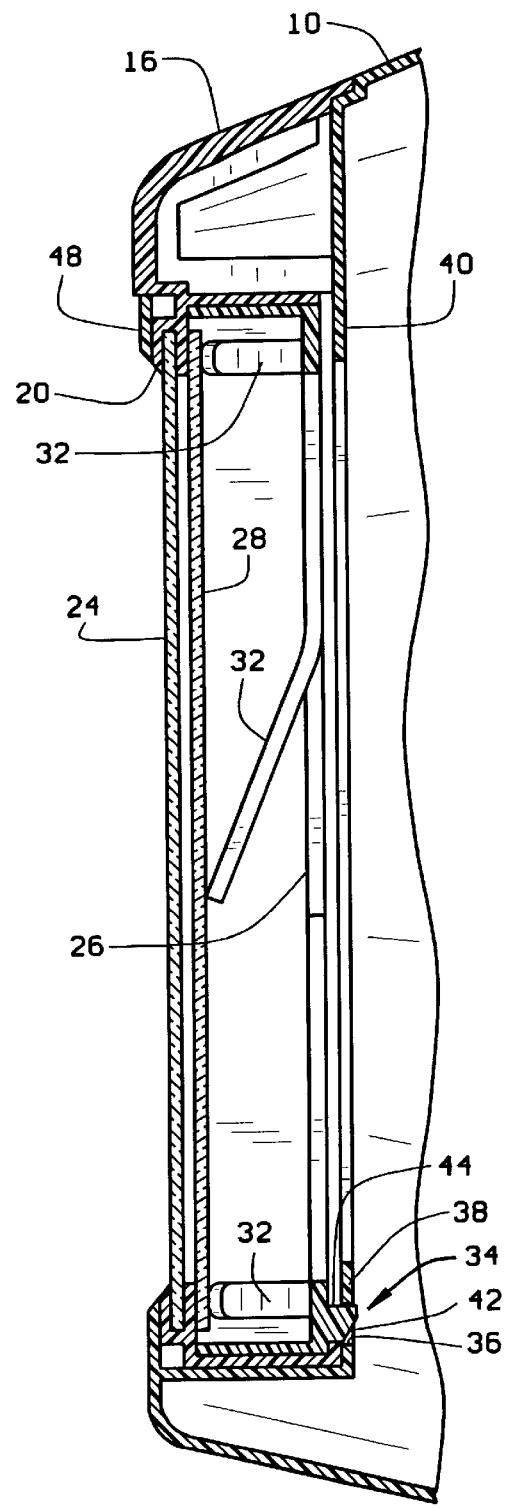
FIG. 8 is a partial cross-sectional view of the lens cartridge assembled with the welding helmet.

As shown in FIGS. 5–8, the cartridge 12 includes a locating nib 34 which provides a second mechanical interlock and which positively mechanically retains the cartridge assembly 12 within slot 14 by engaging with hole 36. Hole 36 is best depicted in FIGS. 2 and 8 and is in a tab 38 which extends inwardly of the rear picture frame border 40 of slot 14. This tab 38 provides a convenient finger grab for a welder to release locating nib 34 from hole 36 so that cartridge 12 may be slidingly removed from slot 14. As shown in FIG. 8, the locating nib 34 has a sloped leading edge 42 and a flattened trailing edge 44 which facilitate the sliding engagement of the cartridge assembly 12 by providing a ramped surface for deflecting tab 38 as the cartridge assembly 12 first contacts it while at the same time providing a positive mechanical interlocking between the parts as the locating nib 34 fully engages hole 36.

As perhaps best shown in FIG. 8, frame assembly 26 is readily captured within cartridge assembly 12 and retained from being accidentally dislodged by the fact of rear picture frame border 40 overlapping the outer periphery of frame assembly 26 thereby making it mechanically impossible for the frame assembly 26 to move backward through the cartridge opening 46 of slot 14. Similarly, a front picture frame border 48 surrounds the front of cartridge opening 46 and extends inwardly along the periphery thereof to provide a mechanical constraint against picture frame member 22 as an aid in preventing inadvertent movement of cartridge 12 through the front of opening 46. Thus, cartridge 12 is mechanically interlocked in place with a locating nib 34 and receiving hole 36 but also mechanically held in place by the front and rear picture frame borders 40, 48 which mechanically capture and positively engage lens cartridge assembly 12 to prevent its movement with respect to the welding helmet 10. This thereby provides a solid mechanical structure sufficient to withstand impact in the face plate area and prevent inadvertent or accidental dislodging of the cartridge 12 which might pose a safety hazard to the wearer.

Various changes may be envisioned by those of ordinary skill in the art to the preferred embodiments disclosed herein. However, those changes and modifications should be considered as part of the invention which is limited only by the scope of the claims appended hereto and their legal equivalents.

What is claimed is:

1. A welding helmet having a removable face plate assembly, said helmet having a slot for receiving said face plate assembly, said face plate assembly comprising a cartridge for insertion into said helmet slot and a frame for holding a plurality of lenses therein, said frame being received by said cartridge.

2. The welding helmet of claim 1 wherein the cartridge includes a face lens, said face lens being slideably received by said cartridge to accommodate replacement thereof.

3. The welding helmet of claim 2 further comprising a first mechanical interlock between said frame and said cartridge, said first interlock releasably holding said frame in said cartridge.

4. The welding helmet of claim 3 further comprising a second mechanical interlock between said cartridge and said helmet, said second interlock releasably holding said cartridge in said helmet.

5. The welding helmet of claim 4 further comprising a plurality of retention clips for holding said plurality of lenses within said cartridge.

6. The welding helmet of claim 5 wherein said first interlock comprises at least one integrally formed tab, and each tab having an associated slot for receiving its associated tab, each of said tabs being positioned on one of said frame or cartridge and its associated slot being formed on the other of said frame or cartridge.

7. The welding helmet of claim 6 wherein said second interlock comprises at least one integrally formed nib, and each nib having an associated hole for receiving its associated nib, each of said nibs being positioned on one of said cartridge or helmet and its associated hole being formed on the other of said cartridge or helmet.

8. The welding helmet of claim 7 wherein said plurality of retention clips comprise a plurality of fingers integrally formed in said frame said fingers being biased into a position so that insertion of said frame into said cartridge holding at least one lens therein deflects said finger s to thereby hold said lens within said cartridge.

9. The welding helmet of claim 8 wherein said welding helmet, cartridge, and frame are all integrally formed plastic parts.

10. The welding helmet of claim 8 wherein said cartridge includes a picture frame slot for receiving said face lens, said face lens being slid into said picture frame slot from a side thereof that is covered by a side of said helmet slot as said cartridge is inserted into said helmet so that said face lens is fully captured by said cartridge and prevented from removal without said cartridge being separated from said helmet.

11. A welding helmet having a removable multi-lens cartridge, said cartridge having a face plate and including a frame for removably securing at least one additional lens inside said cartridge so that said lenses may be readily replaced or exchanged, the cartridge including the face plate, the frame and the at least one additional lens which are all secured together as a single unit and are removable from the helmet as a single unit.

12. The welding helmet of claim 11 further comprising a mechanical stop for indexing said cartridge to said helmet at a home position for proper viewing through said lenses as said helmet is worn by a user.

13. The welding helmet of claim 12 wherein said cartridge includes a second frame for securing said additional lenses inside said cartridge, said second frame being removable from said cartridge and including a mechanical stop for securing said removable frame inside said cartridge.

14. The welding helmet of claim 13 wherein said removable frame further comprises a plurality of fingers for urging said additional lenses into position inside said cartridge.

15. The welding helmet of claim 14 wherein said cartridge includes a slot within which said face plate is slideably received, and which slot has an open side which is covered by said helmet as said cartridge is secured to said helmet.

16. The welding helmet of claim 15 wherein said cartridge face plate serves as a helmet face plate, and is positioned accordingly, as said cartridge is secured to said helmet.

17. The welding helmet of claim 16 wherein said helmet/cartridge mechanical stop comprises a nib and hole and the frame/cartridge mechanical stop comprises a plurality of tabs and slots.

18. In a welding helmet, the improvement comprising a removable lens cartridge, said cartridge including a face plate and a carrier for at least one additional lens positioned adjacent said face plate, said cartridge including the face plate, the carrier and the at least one additional lens which are all secured together as a single unit and are slideably received in and removable from said helmet as a single unit.

19. The welding helmet of claim 18 wherein said cartridge comprises a frame releasably secured to said cartridge, said frame including a plurality of fingers for urging said additional lenses adjacent said face plate.

20. The welding helmet of claim 19 further comprising a mechanical catch between said frame and said cartridge, and between said cartridge and said helmet.

21. The welding helmet of claim 20 wherein said cartridge further comprises a picture frame slot within which said face plate is slideably received and held in place, said slot having an opening which is covered by said helmet as said cartridge is secured within said helmet.

22. The welding helmet of claim 21 wherein said helmet includes an external slot, said external slot having an opening at its upper edge for receiving and holding said cartridge while being accessible from outside said helmet.

23. The welding helmet of claim 22 wherein said external slot comprises a picture frame slot.

24. The welding helmet of claim 23 wherein said mechanical catch between the cartridge and the helmet comprises a nib on said frame and a hole in said helmet, so that as said frame is mounted within said cartridge to form a cartridge assembly, said cartridge assembly may be mechanically latched within said helmet.

\* \* \* \* \*

UNITED STATES PATENT AND TRADEMARK OFFICE
CERTIFICATE OF CORRECTION

PATENT NO.  : 6,151,711
DATED       : November 28, 2000
INVENTOR(S) : David B. Edwards It is certified that error appears in the above-identified patent and that said Letters Patent is hereby corrected as shown below:

Column 4,
Line 34, replace "said finger s" with -- said fingers --.

Column 6,
Line 4, replace "Th e welding helmet" with -- The welding helmet --.
Line 15, replace "a n d the helmet" with -- and the helmet --.

Signed and Sealed this

Twenty-fifth Day of September, 2001

Attest:

NICHOLAS P. GODICI
Attesting Officer  Acting Director of the United States Patent and Trademark Office